US00PP37818P2

(12) United States Plant Patent
O'Connell

(10) Patent No.: US PP37,818 P2
(45) Date of Patent: Oct. 20, 2026

(54) ***GRAPTOSEDUM* PLANT NAMED 'JOKER'**

(50) Latin Name: ***Graptosedum* hybrid**
Varietal Denomination: JOKER

(71) Applicant: Altman Specialty Plants llc, Vista, CA (US)

(72) Inventor: Renee O'Connell, Pala, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/264,352

(22) Filed: Jul. 9, 2025

(51) Int. Cl.
*A01H 5/02* (2018.01)
*A01H 6/32* (2018.01)

(52) U.S. Cl.
USPC ..... Plt./479
CPC ..... *A01H 6/32* (2018.05); *A01H 6/328* (2018.05)

(58) Field of Classification Search
USPC ..... Plt./479
CPC ..... A01H 5/02
See application file for complete search history.

(56) References Cited

PUBLICATIONS https://www.pinterest.com/pin/38773246782998265/; Dec. 29, 2020; 1 page.*
https://www.facebook.com/groups/393923344897048/posts/1546014423021262/; Apr. 26, 2025; 3 pages.*

* cited by examiner

*Primary Examiner* — Kent L Bell

(57) ABSTRACT

A new and distinct cultivar of *Graptosedum* plant named 'JOKER' is disclosed, characterized by clusters of variegated stem rosettes of powder blue with creamy yellow margins. The new cultivar is hardy in full sun, relatively fast growing, branching prolifically to form clusters. The new cultivar is a *Graptosedum*, typically produced as a container plant for the patio or as landscape plants, as well as a cultivar of ornamental purposes.

1 Drawing Sheet

Latin name of the genus and species: *Graptosedum* hybrid.

Variety denomination: 'JOKER'.

BACKGROUND OF THE INVENTION

The new cultivar, *Graptosedum* 'JOKER', is the product of a planned breeding program. The new variety originated as a naturally occurring whole plant mutation of the proprietary, unpatented, seed parent, *Graptosedum* 'Ghosty'. The new cultivar 'JOKER' was discovered by the inventor, Renee O'Connell, in July 2020, in Vista, California, at a commercial greenhouse.

Asexual reproduction of the new cultivar 'JOKER' was first performed in September 2020 in Vista, California, at a commercial greenhouse, by terminal vegetative cuttings. *Graptosedum* 'JOKER' has since asexually produced multiple generations and has shown that the unique features of this cultivar are stable and reproduced true to type.

SUMMARY OF THE INVENTION

The cultivar 'JOKER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JOKER'. These characteristics in combination distinguish 'JOKER' as a new and distinct *Graptosedum* cultivar:

1. The new cultivar *Graptosedum* 'JOKER' forms clusters of variegated stem rosettes.
2. *Graptosedum* 'JOKER' exhibits leaves with a background of clouded powder blue, with margins of creamy yellow, producing a plant for use in small dish gardens, as well as larger container gardens.
3. As *Graptosedum* 'JOKER' is a mutation of *Graptosedum* 'Ghosty', it exemplifies the same hardiness to near 0° C. and can be used in full sun as well.
4. *Graptosedum* 'JOKER' is relatively fast growing, branching prolifically to form clusters, enhancing propagation in a commercial nursery environment.

PARENTAL COMPARISON

Plants of the new cultivar are similar to plants of the parent, in most horticultural characteristics, however, plants of the new cultivar differ in the following;

1. *Graptosedum* 'JOKER' produces variegated leaves, whereas the leaves of *Graptosedum* 'Ghosty' are a solid, clouded powder blue.
2. *Graptosedum* 'JOKER' has a slightly more compact morphology than *Graptosedum* 'Ghosty'.
3. The leaves of *Graptosedum* 'Ghosty' do not blush in bright light, whereas the leaves of *Graptosedum* 'JOKER' blush rose on the variegation when grown in bright light.

COMMERCIAL COMPARISONS

The new cultivar 'JOKER' can be compared to the unpatented commercial variety *Graptosedum* 'Blue Giant'.

Plants of the *Graptosedum* 'Blue Giant' are similar to plants of the new cultivar 'JOKER' in most horticultural characteristics. However, the new cultivar 'JOKER' differs in the following:

1. *Graptosedum* 'JOKER' displays branches of powder blue, variegated with creamy yellow, whereas *Graptosedum* 'Blue Giant' is not variegated.
2. *Graptosedum* 'JOKER' produces a more compact growth habit, whereas *Graptosedum* 'Blue Giant' tends to grow very upright, and becomes very tall.

The new cultivar 'JOKER' can be compared to the unpatented commercial variety *Graptosedum* 'California Sunset'. Plants of *Graptosedum* 'California Sunset' are similar to plants of the new cultivar 'JOKER' in most horticultural characteristics. However, plants of the new cultivar 'JOKER' differ in the following:

1. *Graptosedum* 'JOKER' forms branches of powder blue, variegated with creamy yellow, whereas *Graptosedum* 'California Sunset' forms branches of blue green, sometimes blushed in rose.
2. *Graptosedum* 'JOKER' exhibits a more compact growth than does *Graptosedum* 'California Sunset'.

BRIEF DESCRIPTION OF THE PHOTOGRAPH

The photograph was taken using conventional techniques and equipment. While the colors in the photograph may display variances of color as compared to the living cultivar, due to LRV (light reflectance value), it is as accurate as possible using conventional photographic techniques. Colors in the photograph may appear to differ slightly from the color values cited in the botanical description, which accurately describe the colors of the new cultivar *Graptosedum* 'JOKER'.

The accompanying FIGURE illustrates in full color a plant of *Graptosedum* 'JOKER', at about 6 months, grown at a nursery (approximately 2500-foot candles) in Vista, CA in a 10-inch pot.

DETAILED BOTANICAL DESCRIPTION

In the following description, color references are made to The Royal Horticultural Society Colour Chart, except where general terms of ordinary dictionary significance are used. The following observations and measurements describe 'JOKER' plants in a commercial greenhouse in Vista, California. Temperatures ranged from 1° C. to 33° C. night and day. No artificial light, photoperiodic treatments or chemical treatments were given to the plants. Natural light conditions were approximately 2500 fc of light. Measurements and numerical values represent averages of typical plant types. Botanical classification: *Graptosedum* hybrid 'JOKER'.

PROPAGATION

Type of propagation typically used: Terminal vegetative cuttings.

Time to initiate roots: About 10 days at approximately 24° C.

Root description: Fibrous.

PLANT

Age of plant described: Approximately 4 months from a cutting.

Container size of the plant described: 5-inch.

Growth habit: Central clump of rosettes, trailing with age.

Height: Approximately 8 cm to top of highest leaf.

Plant spread: Approximately 15 cm. Plant comprised of 4 main stems.

Branching characteristics: 4 rosettes produced from a pinch. Un-pinched rosettes produce 1 to 2 rosettes.

Stem:

*Length*.—About 5 cm at this age.
*Diameter*.—About 8 mm.
*Texture*.—Glabrous.
*Color*.—Near RHS Greyed-Green 192A.
*Internode length*.—2 to 4 mm.

Foliage:

*Arrangement*.—Whorled.
*Average length*.—2.5-3.6 cm.
*Average width*.—1.5 to 2 cm.
*Width at base*.—Average 1 cm.
*Aspect of leaf*.—Slight upward curve.
*Leaf thickness*.—9 mm.
*Shape of blade*.—Oblate to nearly spatulate.
*Apex*.—Mucronate.
*Base*.—Attenuate
*Margin*.—Entire.
*Texture of top surface*.—Glabrous. Slightly glaucous.
*Texture of bottom surface*.—Glabrous. Slightly glaucous.
*Quantity of leaves per plant*.—Approximately 20 to 30 per stem.
*Color*.—Young foliage upper side: RHS Greyed-Red 182C. Center strip Greyed-Green 191C. Margins lightly flushed Yellow 2D. Young foliage under side: RHS Greyed-Red 182C. Center strip Greyed-Green 191C. Margins lightly flushed Yellow 2D. Mature foliage upper side: RHS Greyed-Green 191A, fading to 191B towards margins. Center strip Greyed-Green 191C. Margins Yellow 2D. Very light overall tinge Greyed-Red 182D. Mature foliage, under side: RHS Greyed-Green 191A, fading to 191B towards margins. Center strip Greyed-Green 191C. Margins Yellow 4D. Very light overall tinge Greyed-Red 182D.

FLOWER

Not observed.

REPRODUCTIVE ORGANS

Not observed.

OTHER CHARACTERISTICS

Fruits and seeds: Not observed.

Temperature tolerance: Tolerates temperatures from approximately 0° C. to at least 32° C.

Disease/pest resistance: *Graptosedum* are not typically susceptible to diseases and pests. Fungal diseases (*Anthracnose, Cercospora* or *Alternaria*) can occur with excess moisture. Mealybug (*Pseudococcidae* spp.), spider mites (*Tetranychidae* spp.) and scale insects (*Hemiptera* spp.) can be found on *Graptosedum*. Neither resistance or susceptibility to typical diseases and pests of *Graptosedum* has been observed.

Drought tolerance: Tolerates at least 2 weeks of high temperatures without supplemental water, showing no serious damage to plant.

What is claimed is:

1. A new and distinct cultivar of *Graptosedum* plant named 'JOKER' as herein illustrated and described.

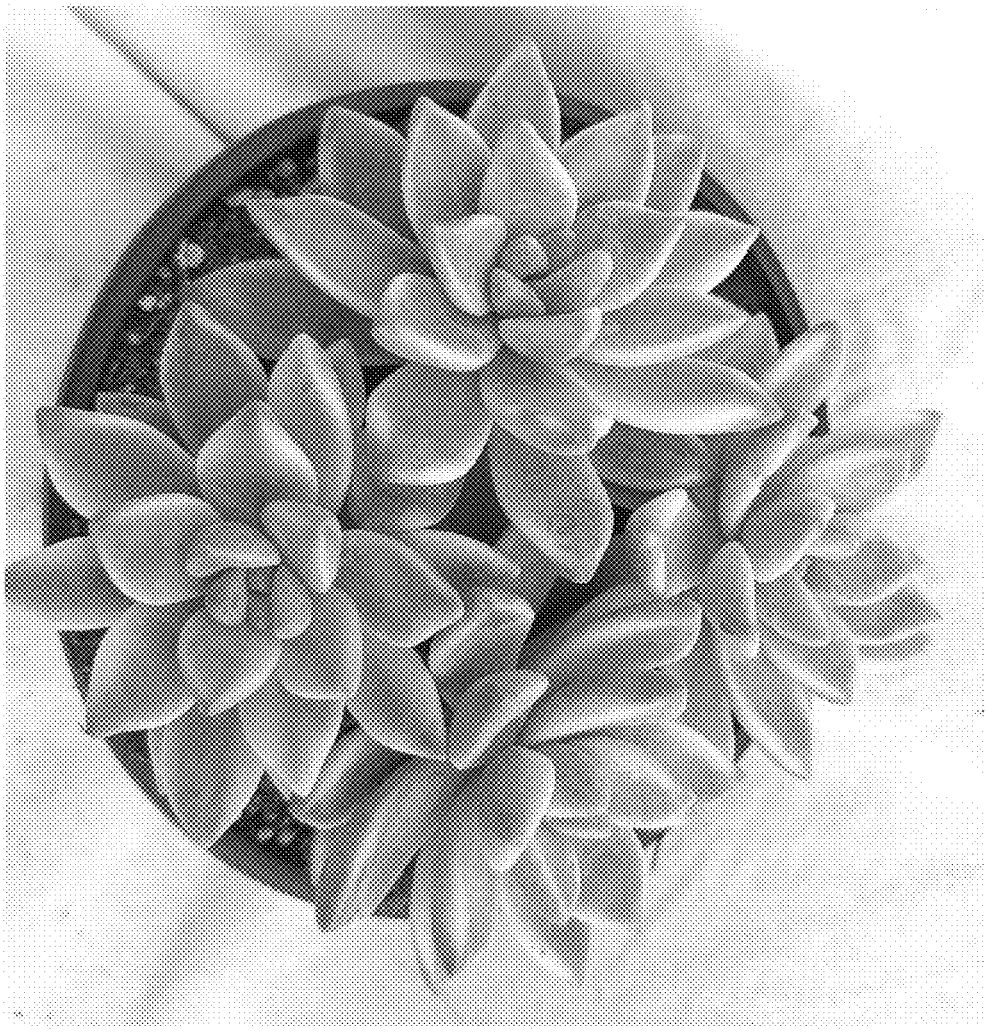

* * * * *